United States Patent [19]

Feldman

[11] 4,409,406

[45] Oct. 11, 1983

[54] PROCESS FOR RECOVERING ETHANOL FROM DILUTE AQUEOUS SOLUTIONS EMPLOYING LIQUID EXTRACTION MEDIA

[75] Inventor: Julian Feldman, Cincinnati, Ohio

[73] Assignee: National Distillers and Chemical Corporation, New York, N.Y.

[21] Appl. No.: 382,544

[22] Filed: May 27, 1982

Related U.S. Application Data

[62] Division of Ser. No. 305,884, Sep. 28, 1981, Pat. No. 4,346,241.

[51] Int. Cl.$^3$ .................... C07C 29/76; C07C 29/80; C07C 29/82; C07C 29/86
[52] U.S. Cl. ................................ 568/916; 568/913; 568/918
[58] Field of Search ...................... 568/916, 918, 913

[56] References Cited

U.S. PATENT DOCUMENTS

| 1,911,829 | 5/1933 | Lebo .................................. 568/918 |
| 2,140,694 | 12/1938 | Evans ................................. 568/916 |
| 2,510,806 | 6/1950 | Egberts et al. .................. 568/918 |
| 2,582,214 | 1/1952 | Twigg ............................... 568/916 |
| 2,597,009 | 5/1952 | Lobo et al. ....................... 568/916 |
| 4,260,836 | 4/1981 | Levy ................................. 568/918 |
| 4,308,106 | 12/1981 | Mannfeld ..................... 203/DIG. 4 |

FOREIGN PATENT DOCUMENTS

| 38668 | 10/1981 | European Pat. Off. ........... 568/913 |
| 49-20108 | 2/1974 | Japan ................................ 568/916 |
| 50-21443 | 7/1975 | Japan ................................ 568/913 |
| 2059787 | 4/1981 | United Kingdom ............... 568/913 |

OTHER PUBLICATIONS

Roddy, "Ind. Eng. Chem. Process Des. Dev.", vol. 20, No. 1, 1981, pp. 104–108.

Primary Examiner—J. E. Evans
Attorney, Agent, or Firm—Kenneth D. Tremain

[57] ABSTRACT

A thermally efficient process for recovering ethanol present in dilute aqueous solution is disclosed which comprises contacting said dilute aqueous ethanol solution with at least one inert extractant which is liquid at ambient temperature and pressure, said extractant being selected from the group consisting of unsubstituted and substituted cyclic secondary amines and unsubstituted and substituted aromatic cyclic amines having a distribution coefficient of at least about 0.70 or a separation factor of at least about 1.0. The invention further provides a process for obtaining substantially anhydrous ethanol from a dilute aqueous ethanol solution in which the ethanol stream is subjected to liquid-liquid extraction to provide an ethanol-poor raffinate phase and an ethanol-rich extract phase, the ethanol present in said latter phase is concentrated in a rectifing column to provide an aqueous ethanol of high proof and the concentrated ethanol is azeotropically distilled in an anhydrous column operated under substantially superatmospheric pressure with thermal values recovered from said anhydrous column being used to satisfy part of all of the thermal operating requirements of the rectifying column.

17 Claims, 4 Drawing Figures

PROCESS FOR RECOVERING ETHANOL FROM DILUTE AQUEOUS SOLUTIONS EMPLOYING LIQUID EXTRACTION MEDIA

This is a division of application Ser. No. 305,884, filed Sept. 28, 1981 now U.S. Pat. No. 4,346,241.

BACKGROUND OF THE INVENTION

1. Field of the Invention

This invention relates to the recovery of ethanol from dilute aqueous solutions by liquid-liquid extraction employing a variety of liquid extraction media, and is especially applicable to recovering and concentrating ethanol present in the dilute aqueous solutions obtained by fermentation.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity consumed and versatility in product synthesis.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of sugar to a dilute solution of ethanol ("beer") and the separation and concentration of the ethanol by distillation, have been modified in numerous ways to achieve improvements in product yield, production rates and so forth (see, for example, U.S. Pat. No. 3,236,740 and the booklet "Industrial Alcohol by Continuous Fermentation and Vacuum Distillation With Low Energy Consumption," of Chemapec, Inc., Woodbury, N.Y.). For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol and enhance the standing of the ethanol as an economically viable replacement for petroleum based raw materials. To date, however, relatively little concern has been given to the energy and raw material requirements for manufacturing ethanol from biomass and consequently, little effort has been made to minimize the thermal expenditure and waste of raw materials incurred in carrying out any of the aforesaid discrete operations involved in the manufacture of ethanol from vegetative sources.

Recovery of fermentation ethanol by distillation accounts for a large amount of the overal energy requirements for conversion of biomass to concentrated ethanol. Roddy, "Distribution of Ethanol-Water Mixtures to Organic Liquids," Ind. Eng. Process Des. Dev., 1981, 20, 104–108, proposes the use of organic solvent extraction followed by gas stripping of ethanol from the organic phase as a substitute for distillation in alcohol separation and concentration. According to this publication, the hydrocarbons as a class are poor extractants for ethanol but tend to give the highest separation factors because of their even poorer solvent properties for water. A variety of ethanol extractants were evaluated including cyclohexane, benzene, toluene, xylene, ethylbenzene, chloroform, 1-octanol, 2-ethyl-1-butanol, n-butyl acetate and tri-n-butyl phosphate, and their distribution coefficients K (i.e., the value obtained by dividing the concentration of ethanol in the organic layer by the concentration of ethanol in the aqueous layer) were measured. Roddy discloses that the highest distribution coefficient (designated by the author as $D_{EtoH}$) was $6.9 \times 10^{-1}$ (measured at 25° C.) which was obtained for 2-ethyl-1-butanol. The only nitrogen-containing extractants evaluated by Roddy, Amberlite XLA3, a primary amine from Rohm and Haas, and Adogens 364 and 464, tertiary and quaternary amines from Ashland Chem., had much lower distribution coefficients, measuring $4.4 \times 10^{-3}$, $1.7 \times 10^{-2}$ and $4.8 \times 10^{-1}$ respectively.

SUMMARY OF THE INVENTION

In accordance with the present invention, ethanol present in dilute aqueous solution is recovered therefrom in more concentrated form by contacting said dilute aqueous ethanol solution with at least one inert extractant which is liquid at ambient temperature and pressure, said extractant being selected from the group consisting of unsubsitituted and substituted cyclic secondary amines and unsubstituted and substituted aromatic cyclic amines having a distribution coefficient at ambient temperature and pressure of at least about 0.70.

The use of an ethanol extractant of the aforesaid type combined with removal of the ethanol from the extractant by distillation to provide anhydrous ethanol as more fully described herein can reduce the heat inputs required to obtain anhydrous ethanol from dilute solutions by substantial amounts. For example, the heat inputs required for recovery of anhydrous ethanol from 4.5% and 8% by weight aqueous ethanol solutions employing conventional distillation procedures will frequently average about 25,000 and 13,000 BTU/gal., respectively. However, employing 5,6,7,8-tetrahydroquinoline (THQ) which has a distribution coefficient at ambient temperature and pressure of about 1.05 as extractant, the heat inputs can be reduced to 15,590 and 11,540 BTU/gal., respectively. In the case of fermentation ethanol, the additional capital investment required to implement the liquid-liquid extraction process of the present invention can be more than offset by employing a single stage, in contrast to a multistage, fermentation system since the thermal savings which can be realized by the practice of this invention will often be far more pronounced with aqueous ethanol feeds of relatively low concentration, e.g., from about 2–6% by weight, than with feeds of relatively high ethanol concentration e.g., from about 6–12% by weight.

While the process of this invention is especially advantageous when applied to the recovery and concentration of ethanol produced by fermentation, the process is similarly beneficial when applied to dilute aqueous ethanol streams obtained from other processes, e.g., from the catalytic hydration of ethylene.

DESCRIPTION OF THE PREFERRED EMBODIMENTS

Figure 1:
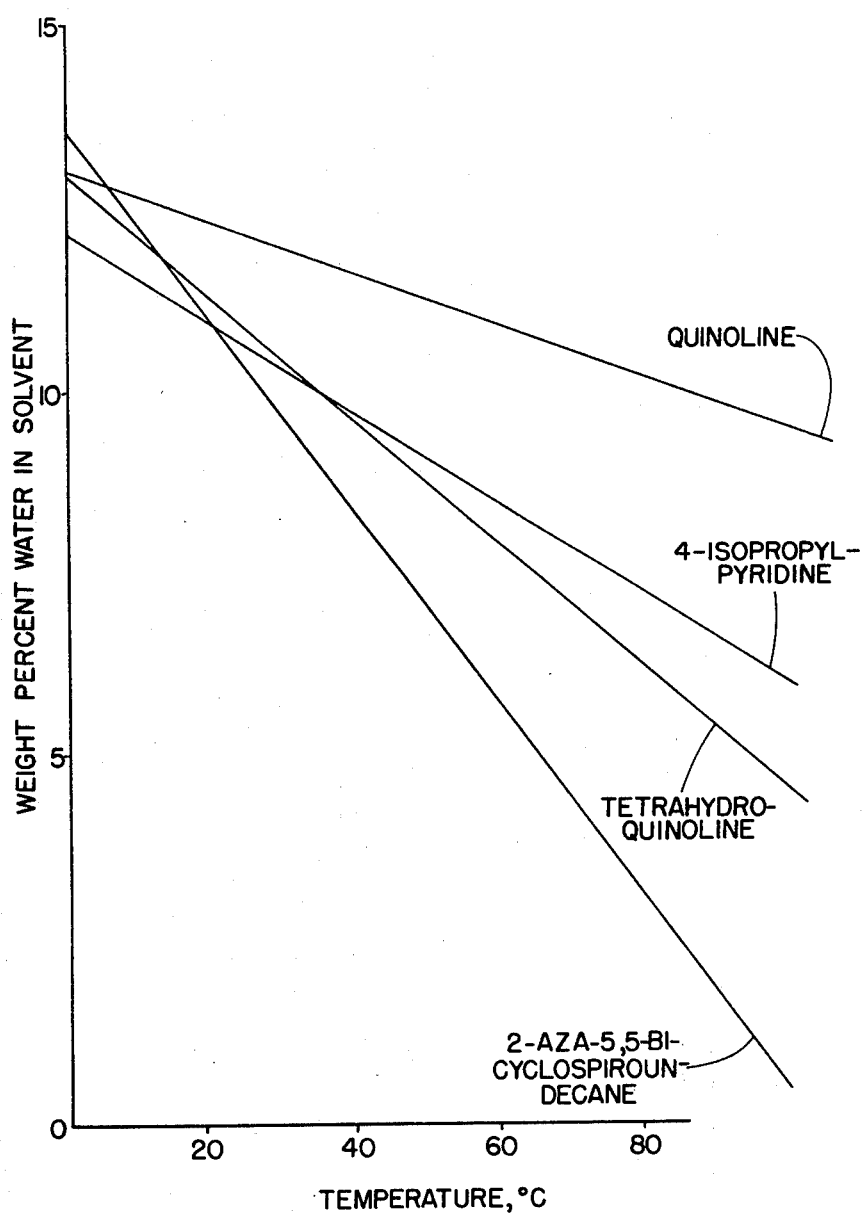
FIG. 1 is a graph showing the solubility of water in a number of extractants herein at temperatures of from 0° C. to 80° C.

The ethanol extractant herein is selected from among any of the inert, normally liquid unsubstituted and substituted liquid secondary amines, and unsubstituted and substituted aromatic cyclic amines having a distribution coefficient under ambient conditions of at least about 0.70. The distribution coefficient, $K_{EtOH}$, of the extraction solvents herein were measured at ambient temperature and pressure and are calculated by dividing the weight concentration of ethanol in the organic, i.e., extractant, layer by the concentration of ethanol in the aqueous layer. As a class, the cyclic and heterocyclic amines are excellent extractants for ethanol possibly due to the high affinity of the nitrogen for the hydroxylic hydrogen of the ethanol. Whatever, in fact, the explanation for this behavior may be, it is possible employing routine procedures to identify many more members of this class of materials besides those specifically identified hereinafter which possess a $K_{EtOH}$ value of at least about 0.70 at ambient temperature and pressure. Extractants having a $K_{EtOH}$ value of at least about 0.90 and more preferably, above about 1.0, are especially advantageous for use in the present invention. Specific examples of useful extractants, together with their distribution coefficients, are set forth in Table I as follows:

TABLE I

| Extractant | Distribution Coefficient |
|---|---|
| 1,2,3,4-tetrahydroisoquinoline | 1.00 |
| 2-aza-5,5-bicyclospiroundecane | 1.16 |
| quinoline | 1.12 |
| isoquinoline | 0.92 |
| 2,3-cyclopentenopyridine | 1.07 |
| 5,6,7,8-tetrahydroquinoline | 1.05 |
| 2,3-cycloheptenopyridine | 0.76 |
| 4-isopropylpyridine | 1.2 |
| 4-n-propylpyridine | 1.0 |
| 2-n-propylpyridine | 0.97 |
| 4-(3-pentyl)pyridine | 0.82 |

Based purely on operational considerations, it is preferred to employ an extractant having the highest distribution coefficient. In practice, however, the selection of extractant will ordinarily take cost into consideration so that the choice of extractant for a given facility at a given time will represent a balance between the technical effectiveness of the material and its cost.

Another approach toward the selection of extractant makes use of the separation factor (S.F.) which is the ratio of the partition coefficient for $K_{EtOH}$, as previously defined, to water, $K_{H_2O}$ (i.e., the water concentration in the solvent layer divided by the water concentration in the aqueous layer). With the extractants herein, the solubility of water decreases with increasing temperature so $K_{H_2O}$ also decreases. A value of S.F. greater than about 1.0 indicates that the extractant will preferentially dissolve ethanol thereby enriching it relative to water. For a given $K_{EtOH}$, the larger the S.F. the more effective the extractant in the process of this invention. It is preferred to employ an extractant having an S.F. of at least about 5.0 at 21° C., and more preferably, an S.F. of at least about 20 at 21° C., in the practice of this invention.

The solubility of water in the most effective extractants (quinoline, 2-aza-5,5-bicyclospiroundecane, 4-isopropylpyridine, and tetrohydroquinoline) was experimentally determined over the range 0° C. to 80° C. by titrating water into a stirred sample of the extractant. The end point was considered to be a stable cloud point. In all cases the solubility of water decreased with increasing temperature.

The curves plotted from the solubility data are shown in FIG. 1. The equations for these curves, derived by linear regression, are:

| | |
|---|---|
| quinoline | $W = 21.1e^{-0.0082T}, (r = 0.968)$ |
| 2-aza-5,5-bicyclospiroundecane | $W = 23.7e^{-0.031T}, (r = .978)$ |
| 4-isopropylpyridine | $W = 17e^{-0.015T}, (r = .970)$ |
| 5,6,7,8-tetrahydroquinoline | $W = 20.8e^{-0.02T}, (r = .942)$ | where:
W = weight % of water
T = temperature in °C.
r = correlation coefficient

Extractions were made at 60° C. to experimentally determine the temperature effect on the $K_{EtOH}$ and S.F. for quinoline, 5,6,7,8-tetrahydroquinoline, and 2-aza-5,5-bicyclospiroundescane. As shown in Table II below, both $K_{EtOH}$ and S.F. increased with temperature while $K_{H_2O}$ decreased. The concentration of ethanol relative to water in the raffinate was enriched from 4.5% to 65% with decahydroquinoline.

TABLE II

EFFECT OF TEMPERATURE ON EXTRACTION

| Solvent | Temp. °C. | $K_{EtOH}$ | $K_{H_2O}$ | S.F. | Wt. % EtOH in Extract (Relative to H$_2$O) |
|---|---|---|---|---|---|
| Quinoline | 21 | 1.00[1] | 0.17 | 5.8 | 20 |
| | 60 | 1.12 | 0.15 | 7.5 | 26 |
| 2-Aza-5,5-bicyclo- | 21 | 0.88 | 0.13 | 6.8 | 25 |
| spiroundecane | 60 | 0.97 | .043 | 23 | 54 |
| Decahydroquinoline | 21 | 0.94 | .047 | 20 | 54 |
| | 60 | 1.04 | .025 | 42 | 60 |

[1]Value obtained in multistage extraction.

In addition to these extractions, another series of extractions were carried out at 85° C. and 100° C. Table III below summarizes the observed data.

TABLE III

EFFECT OF TEMPERATURE ON EXTRACTION

| Solvent | Temp. °C. | $K_{EtOH}$ | $K_{H_2O}$ | S.F. | Wt. % EtOH in Extract (Relative to H$_2$O) |
|---|---|---|---|---|---|
| Quinoline | 21 | 1.00 | 0.17 | 5.8 | 20 |
| | 60 | 1.12 | 0.15 | 7.5 | 26 |
| | 85 | 1.20 | 0.14 | 8.8 | 28 |

TABLE III-continued
EFFECT OF TEMPERATURE ON EXTRACTION

| Solvent | Temp. °C. | $K_{EtOH}$ | $K_{H_2O}$ | S.F. | Wt. % EtOH in Extract (Relative to H$_2$O) |
|---|---|---|---|---|---|
|  | 100 | 1.22 | 0.13 | 9.4 | 28 |
| 2-Aza-5,5-bicyclo- | 21 | 0.88 | 0.13 | 6.8 | 25 |
| spiroundecane | 60 | 0.97 | 0.043 | 23 | 54 |
|  | 85 | 0.88 | 0.021 | 42 | 65 |
| 5,6,7,8-tetra- | 21 | 1.05 | 0.20 | 5.3 | 20 |
| hydroquinoline | 85 | 1.30 | 0.072 | 18 | 41 |
|  | 100 | 1.32 | 0.056 | 24 | 49 |
| Decahydro- | 21 | 0.94 | 0.047 | 20 | 54 |
| quinoline | 60 | 1.04 | 0.025 | 42 | 65 |
|  | 85 | 0.92 | 0.017 | 54 | 71 |
| 1,9-Octahydro- | 21 | 1.15 | 0.37 | 3.1 | 11 |
| quinoline | 85 | 1.44 | 0.059 | 24 | 49 |

As shown in these data, the highest S.F. was 54, obtained at 85° C. with decahydroquinoline which enriched the ethanol from 4.5% to 71% relative to water. With the solvents tested, high S.F. values resulted more from the decrease in $K_{H_2O}$ with increasing temperature rather than an increase in $K_{EtOH}$.

The highest $K_{EtOH}$ was 1.44, obtained with 1,9-octahydroquinoline at 85° C., the $K_{EtOH}$s for decahydroquinoline and 2-aza-5,5-bicyclospiroundecane peaked at 60° C. and decreased at higher temperatures. Both quinoline and tetrahydroquinoline $K_{EtOH}$s increased with temperature until 85° C. but had the same value at 100° C. It was not determined if maximum $K_{EtOH}$s existed between 85° and 100° C.

The $K_{EtOH}$ for delta-1,9-octahydroquinoline, a by-product of the synthesis of decahydroquinoline, was not determined at 100° C. because of insufficient material. The solubility of water in delta-1,9-octahydroquinoline was determined from 0° C. to 80° C. The equation derived is:

$$W = 4.9e^{-0.029T}, (r=0.997)$$

where
W = weight % of H$_2$O
T = Temperature in °C.
r = correlation coefficient.

In general, the extraction will be carried out at about the temperature of the aqueous ethanol feed or at elevated temperature approaching the boiling point of the ethanol-extractant mixture. It is, of course, recognized that while elevated temperatures favor greater extraction levels, such can be achieved only with the input of heat which may or may not be available at relatively low cost depending upon the design of other elements of biomass ethanol system.

The quantities of extractant employed herein can vary widely with the extraction effectiveness of a particular solvent, its cost, the volume of dilute aqueous ethanol being processed, flow rates, the number of extraction stages, contact times and similar factors being taken into consideration when determining the optimum quantity of extractant for a given facility.

Figure 2A:
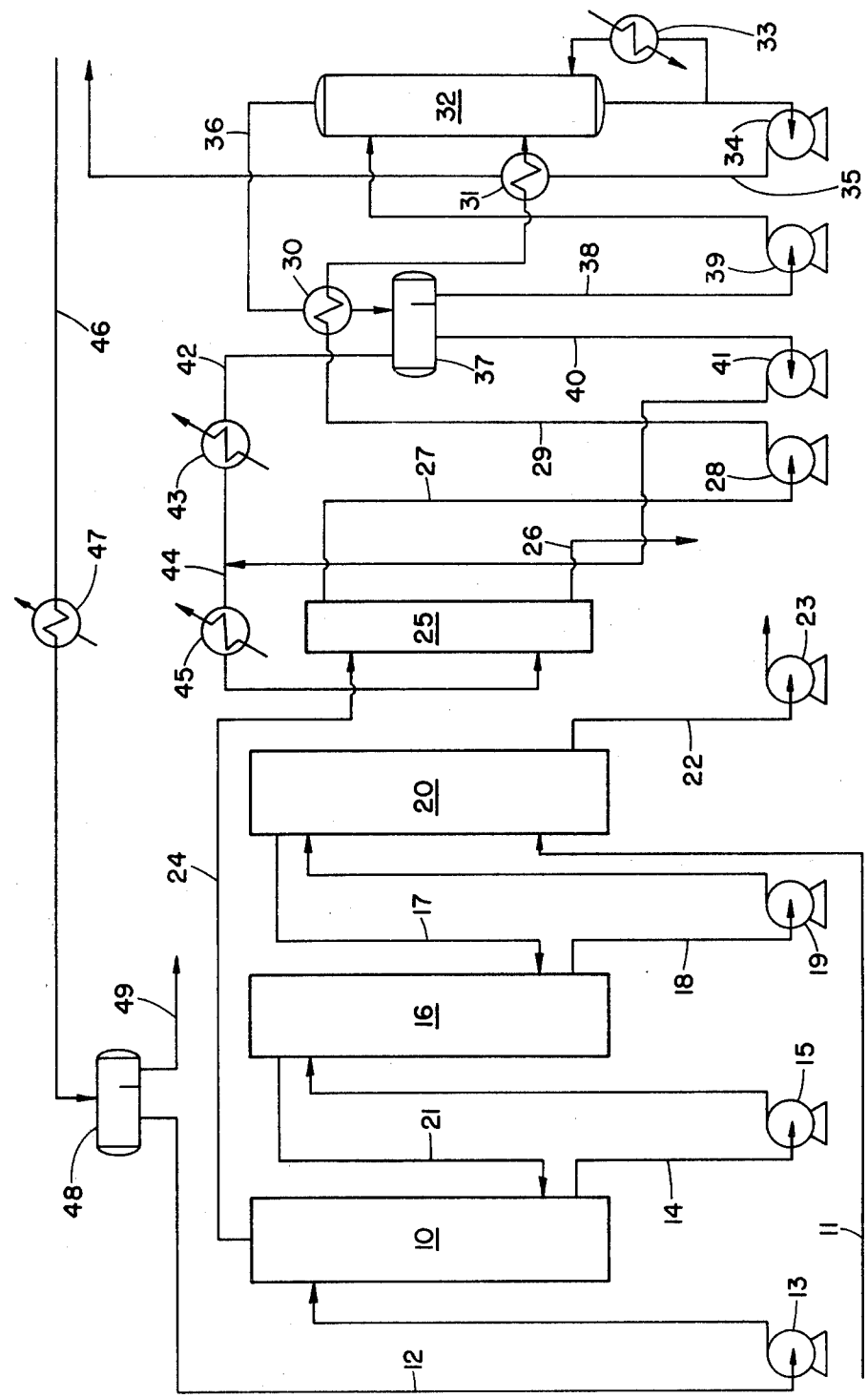
FIG. 2A is a schematic diagram of a multistage, countercurrent liquid-liquid ethanol extraction process is accordance with one embodiment of the present invention

In accordance with FIG. 2A, an aqueous fermentation ethanol feed containing from about 4.5-8 weight percent ethanol is continuously introduced into the bottom of a third rotating disk contactor extraction column 20 through line 11 while 5,6,7,8-tetrahydroquinoline (THQ) extractant is continuously introduced into the top of column 10 through line 12 via pump 13 to effect counter-current extraction of ethanol contained in the feed stream. The ethanol-containing THQ discharged from the bottom of column 10 through line 14 is then introduced via pump 15 into the top of a second rotating disk contactor extraction column 16 to accomplish still further extraction of ethanol with the raffinate discharged from the top of column 20 being delivered by gravity to the bottom of column 16 through line 17. The sequence of extraction is repeated for a third time with the ethanol-containing THQ discharged from the bottom of column 16 through line 18 being introduced via pump 19 to the top of third rotating disk contactor extraction column 20 and the raffinate discharged from the top of column 16 being delivered by gravity to the bottom of column 10 through line 21. The ethanol-containing THQ extractant discharged from the bottom of column 20 through line 22 is then sent by pump 23 to distillation as hereinafter described in FIG. 2B for separation of the ethanol and THQ and recycle of the latter. The extract from column 20 contains ethanol in a concentration of from about 25-35 weight percent relative to water (depending on feed stream concentration and extraction temperature). The raffinate phase from column 10 which contains a small amount of extractant, is introduced through line 24 into the top of extractant recovery column 25 continuously supplied at the bottom thereof with xylene or other THQ extractant through line 44. The aqueous bottoms from column 25 are either discharged to waste through line 26, or, if the residual amounts of solvent therein have no appreciably detrimental affect on fermentation, are recycled. The THQ/xylene mixture discharged from the top of column 25 through line 27 is delivered via pump 28 through line 29 and through condenser 30 to partially condense the overheads from solvent recovery fractionation column 32, through preheater 31 and thereafter into said fractionation column 32 driven with steam supplied through reboiler shell 33. The bottoms recovered from fractionator column 32, containing THQ, are sent via pump 34 through line 35 and through preheater 31 giving up a portion of the thermal values therein to the THQ/ethane entering fractionation column 32 and thereafter to rectifier column feed preheater 50 whose operation is hereinafter described in FIG. 2B. The xylene vapor overheads from column 32 passing through line 36 are partially condensed by the THQ/ethanol/xylene mixture passing through condensor 30, a portion of the condensed xylene in overheads accumulator 37 being recycled through line 38 by pump 39 to the top of column 32 to serve as reflux and the remainder of the partial xylene condensate being recycled through line 40 by pump 41 to be combined with the balance of the xylene passing through line 42 and which has been condensed in overhead condenser 43. The combined xylene streams in line 44 are passed through recycle cooler 45 and thereafter into the bottom of column 25 to effect further recovery of THQ/ethanol from the raffinate phase. THQ recycle extractant from the distillation process described in FIG. 2B passing through line 46 is cooled by solvent recycle cooler 47 and is decanted in solvent recycle decanter 48 to remove excess water therein, the aqueous phase being recycled to distillation through line 49 and the THQ phase being recycled through line 12 via pump 13 to the top of first rotating disk contactor extraction column 10 for use in extracting fresh aqueous ethanol feed.

Figure 2B:
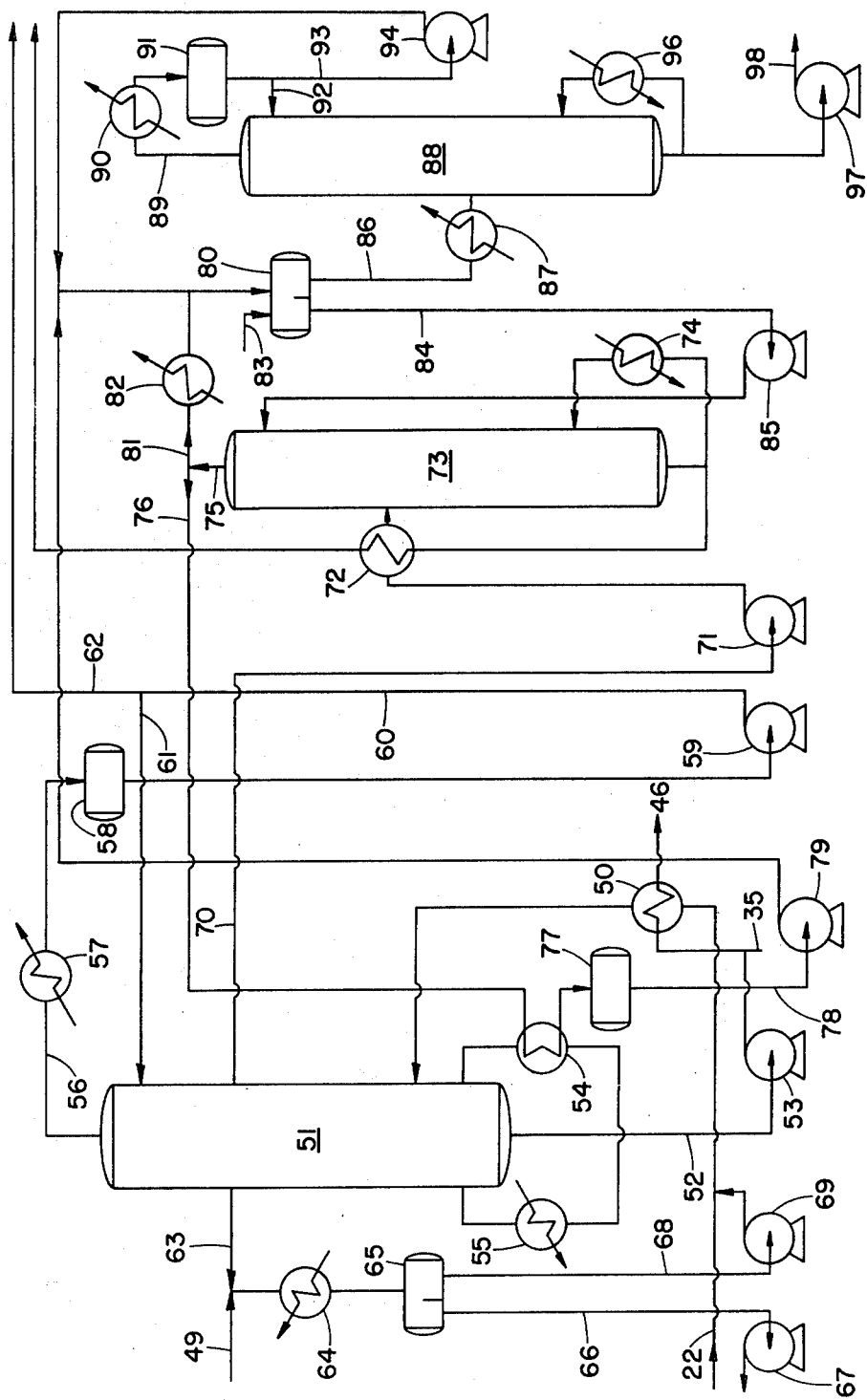
FIG. 2B is a schematic diagram of a distillation process which is integrated with the extraction process of FIG. 1A to provide substantially anhydrous ethanol.

In accordance with FIG. 2B; ethanol-rich THQ extractant in line 22 (i.e., the organic phase from third rotating disk contactor extraction column 20 of FIG. 2A) is passed through rectifier feed preheater 50 where it picks up thermal values from the THQ bottoms forced from rectifier column 51 through line 52 by pump 53 and THQ bottoms forced from fractionation column 32 of FIG. 2A through line 35 by pump 34 thereof. The combined THQ streams are recycled through line 46 of FIG. 2A as previously described. The preheated THQ ethanol stream introduced through line 22 into rectifier column 51 operated at or about atmospheric pressure is heated therein by recovered steam provided to rectifier reboiler shell 54 and steam provided to rectifier trim reboiler shell 55 as demand requires. The THQ bottoms are recovered therefrom through line 52 as previously described and the ethanol vapor overheads are recovered through line 56. Passing through rectifier condenser 57, the condensate enters rectifier reflux drum 58 and is discharged therefrom by pump 59 through line 60 with part of the ethanol being conveyed to storage through line 62 and part being returned as reflux through line 61. A side draw stream withdrawn from rectifier column 51 through line 63 and containing fusel oil is combined with recycle water passing through line 49 of FIG. 2A and after passing through side draw cooler 64 is introduced into side draw decanter 65. The fusel oil phase is decanter 65 is recovered through line 66 and is sent by pump 67 either to separate storage or to storage with the ethanol passing through line 62. The aqueous phase recovered from decanter 65 through line 68 is recycled by pump 69, together with the THQ/ethanol stream passing through line 22, into rectifier column 51. The aqueous ethanol (about 94 weight percent ethanol) recovered from rectifier 51 through line 70 is forced by pump 71 through anhydrous column preheater 72 and into anhydrous column 73 wherein azeotropic distillation is carried out, preferably at substantially superatmospheric pressure, e.g., from about 60 to about 150 psig, and more preferably, from about 80 to about 130 psig. By operating anhydrous column 73 at significantly elevated levels of pressure, a sufficient amount of heat is recoverable from this column to supply a good part, if not all, of the thermal operating requirements of rectifying column 51. Heat is supplied to anhydrous column 73 by liquid recirculating through reboiler 74 supplied with steam. Part of the vapor overhead (azeotrope-forming agent, ethanol and water) passing from anhydrous column 73 through line 75 is conveyed through line 76 giving up heat in reboiler shell 54 to rectifying column liquid recirculating therethrough. The condensed liquid resulting from the passage of anhydrous column overheads through reboiler shell 54 enters drum 77 and is delivered therefrom through line 78 by pump 79 to the top of anhydrous decanter column 80. Another part of the vapor passing from anhydrous column 73 through line 75 is conveyed through line 81 through condenser 82 with the condensate entering decanter 80. Start-up azeotrope-forming agent can be supplied to the system at any convenient point such as through line 83 to decanter 80. The phase in decanter 80 which is rich in azeotrope forming agent is conveyed through line 84 by pump 85 to the top of anhydrous column 73 to provide reflux liquid. The water-rich phase in decanter 80 containing a small amount of ethanol passes through line 86 and through cooler 87 into water stripper column 88 which is driven by steam supplied to reboiler shell 96.

Vapor overheads from water stripper column 88, consisting of azeotrope forming agents, are conveyed through line 89 and passing through stripper condenser 90, are condensed, the condensate passing into stripper column reflux drum 91. Part of the condensed azeotrope-forming agent is returned to column 88 through line 92 to serve as reflux with the remainder of the azeotrope-forming agent being delivered through line 93 by pump 94 to decanter 80. The bottoms from column 88, consisting of clean water, are discharged therefrom by pump 97 through line 98, either to be discarded or recycled as desired.

While any of the azeotrope-forming agents heretofore employed for the anhydrous distillation of ethanol, e.g., benzene, toluene, etc., can be used herein with good results, it is preferred to employ cyclohexane for this purpose especially when anhydrous column 73 is operated under pressure. In the past, it has been proposed to carry out anhydrous distillation of ethanol at elevated pressure employing diethyl ether an an entraining agent. (Moeller et al., *Industrial Engineering Chemistry*, Vol. 43. No. 3, pp. 711–717 (1951); Wentworth et al., *Trans. Am. Inst. Chem. Engrs.*, Vol. 39, pp. 565–578 (1943) and Vol. 36, pp. 785–799 (1940)). However diethyl ether has numerous drawbacks compared to cyclohexane for this purpose. For one thing, much higher anhydrous column operating pressures would be required in order to provide sufficient heat to run a rectifying column when working with diethyl ether. For another, diethyl ether is more hazardous than cyclohexane and reasons of safety alone militate against its use. Moreover, ether gives inferior separation between ethanol and water compared to that provided by cyclohexane.

EXAMPLE

Figure 3:
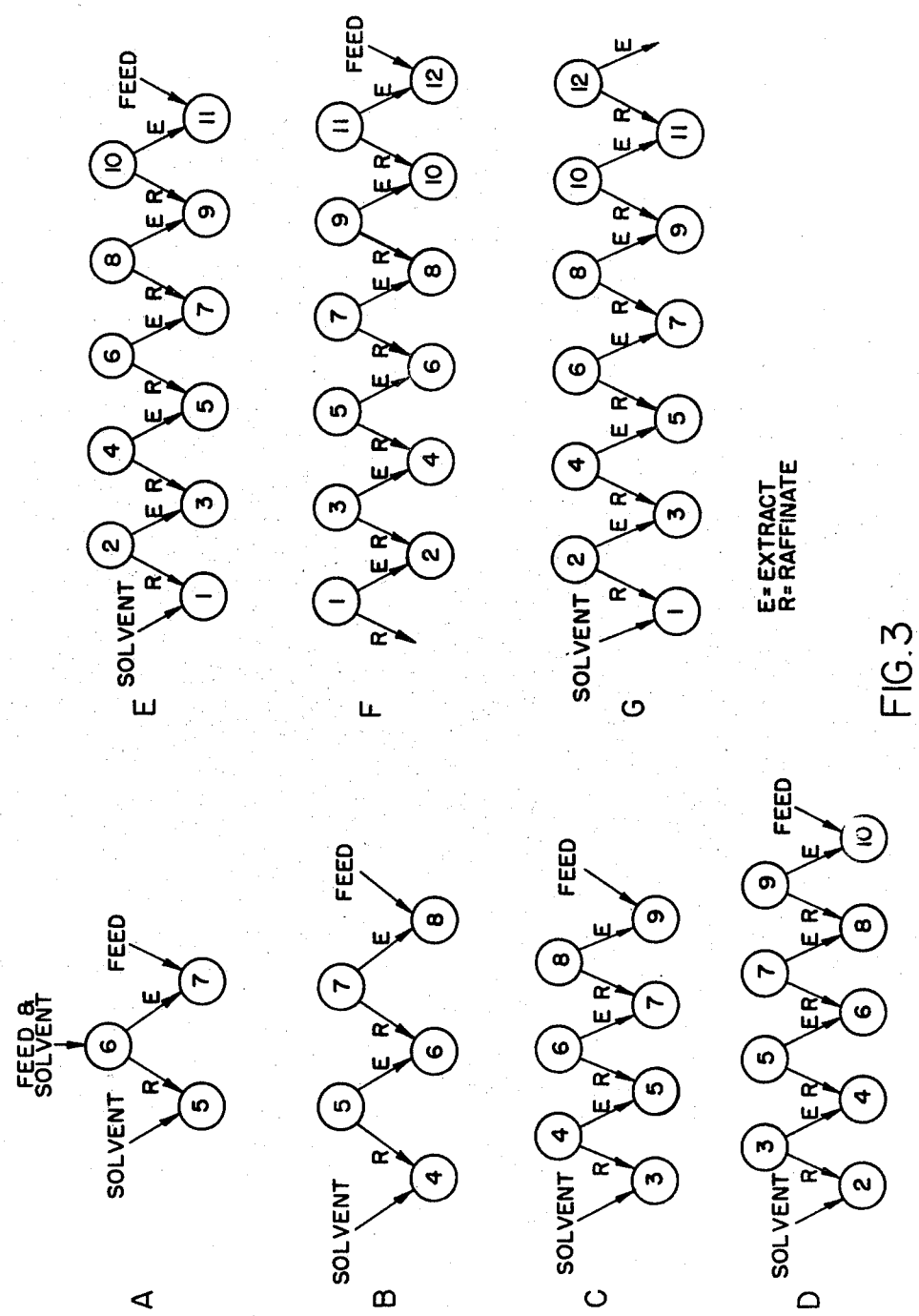
FIG. 3 is a schematic diagram illustrating the process herein on a laboratory scale.

In the schematic diagram illustrated in FIG. 3, a twelve-stage countercurrent extraction system with quinoline (practical grade, saturated with water before use to minimize sorption of water from the aqueous phase) as extractant was employed in a laboratory scale demonstration of the present invention applied to a beer containing about 8 percent ethanol by weight. Equal volumes (100 ml) of beer and extractant were introduced to the system at room temperature.

Start-up required batchwise initiation of the stages to the process as shown in FIG. 3. Feed and solvent were introduced into funnel 6, stage 6 of the extraction system. The funnel was then vigorously shaken and allowed to settle for 10–15 minutes. When phase separation was complete, the extract phase (lower layer) was drawn off and transferred to funnel 7 and the raffinate phase (upper layer) to funnel 5. Fresh extractant was then added to the raffinate in funnel 5 and fresh feed added to the extract in funnel 7. After agitation and settling, the extract from funnel 7 was drawn off and transferred to funnel 8 and the raffinate to funnel 6 in B. The extract from funnel 5 was drawn off and transferred into funnel 6 and the raffinate to funnel 4. Fresh solvent was then added to funnel 4 and fresh feed to funnel 8. This procedure was followed until all twelve funnels were introduced into the system (C, D, E and F). The extract phase from stage N would transfer into stage N+1, and the raffinate phase from stage N would transfer into stage N−1, thereby effecting a countercurrent extraction system. When the system was complete, fresh feed was added to funnel 12 and a raffinate withdrawn from the system from funnel 1 as shown in F. After separation took place, fresh solvent was added to funnel 1 and an extract was withdrawn from the system from funnel 12 as shown in G, such constituting one full cycle of the system.

After 11 full cycles had been completed, the raffinates from cycles 9, 10, and 11 were analyzed for ethanol content by gas-liquid chromatography. While steady-state had not been established in 11 cycles, such was achieved in 15 cycles. Twenty-five ml extract and raffinate samples were then taken from each funnel for analysis. The results showed that 95% of the ethanol present in the feed was recovered in the extract. The complete results are reported in Table IV below. The raffinate samples were analyzed by gas-liquid chromatography using propanol as an internal standard. Since the extract analysis did not use an internal standard, each sample was analyzed three or more times and an average value calculated for ethanol content. This procedure resulted in an error of +9% with a certainty of 95%. A material balance shows that the final extract was 109.5 ml and the final raffinate 90.5 ml.

TABLE IV

TWELVE STAGE COUNTERCURRENT EXTRACTION OF ETHANOL WITH SATURATED QUINOLINE SOLVENT

| Stage | Raffinate ETOH Conc. mmol/ml. | Extract ETOH Conc. mmol/ml. |
|---|---|---|
| 1 | .091 | .099 |
| 2 | .188 | .201 |
| 3 | .287 | .313 |
| 4 | .394 | .426 |
| 5 | .512 | .574 |
| 6 | .620 | .643 |
| 7 | .736 | .775 |
| 8 | .837 | .929 |
| 9 | .960 | 1.025 |
| 10 | 1.088 | 1.175 |
| 11 | 1.259 | 1.340 |
| 12 | 1.331 | 1.480 |

What is claimed is:

1. A process for obtaining substantially anhydrous ethanol from a dilute aqueous ethanol solution thereof which comprises
    (a) contacting the dilute aqueous ethanol solution with an inert organic extractant which is liquid at ambient pressure and temperature in at least one extraction zone for a period of time sufficient to provide a raffinate phase containing significantly less ethanol than the dilute aqueous ethanol feed, and an extract phase containing a significant amount of the ethanol originally present in the dilute aqueous ethanol feed,
    (b) concentrating the extract phase resulting from step (a) in a rectifying column to provide an aqueous ethanol of high proof; and,
    (c) azeotropically distilling the concentrated ethanol resulting from step (b) in an anhydrous column operated under substantially superatmospheric pressure with thermal values recovered from the anhydrous column overheads being used to satisfy part of all of the thermal operating requirements of the rectifying column.

2. The process of claim 1 wherein the dilute aqueous solution of ethanol contains from about 2 to about 12 percent ethanol by weight.

3. The process of claim 1 wherein the dilute aqueous solution of ethanol contains from about 2 to about 6 percent ethanol by weight.

4. The process of claim 2 or 3 wherein the aqueous solution of ethanol is a beer.

5. The process of claim 1 wherein the extractant is selected from the group consisting of unsubstituted and substituted cyclic secondary amines and unsubstituted and substituted aromatic cyclic amines having a distribution coefficient of at least about 0.70.

6. The process of claim 1 wherein the extractant is selected from the group consisting of unsubstituted and substituted cyclic secondary amines and unsubstituted aromatic cyclic amines having a separation factor of at least about 1.0.

7. The process of claim 5 wherein the distribution coefficient of the extractant is at least about 0.90.

8. The process of claim 5 wherein the distribution coefficient of the extractant is at least about 1.0.

9. The process of claim 6 wherein the separation factor of the extractant is at least about 5.0 at 21° C.

10. The process of claim 6 wherein the separation factor of the extraction is at least about 20 at 21° C.

11. The process of claim 5 or 6 wherein the extractant is at least one member of the group consisting of
    1,2,3,4-tetrahydroisoquinoline,
    2-aza-5,5-bicyclospiroundecane,
    quinoline,
    isoquinoline,
    2,3-cyclohexenopyridine
    5,6,7,8-tetrahydroquinoline,
    2,3-cyclopentenopyridine,
    4-isopropylpyridine,
    4-n-propylpyridine,
    2-n-propylpyridine, and
    4-(3-pentyl)pyridine.

12. The process of claim 1 wherein the extractant is saturated with water prior to use.

13. The process of claim 1 wherein the aqueous solution of ethanol is contacted with the extractant in a plurality of countercurrent extraction zones, the raffinate from the last extraction zone is subject to extraction for separation and recovery of the small quantity of extractant therein and the ethanol-containing extract from the last extraction zone is subject to steps (b) and (c).

14. The process of claim 1 wherein the anhydrous column is operated at from about 60 to about 150 psig.

15. The process of claim 1 wherein the anhydrous column is operated at from about 80 to about 130 psig.

16. The process of claim 1 wherein the anhydrous column is operated with cyclohexane as the azeotrope-forming agent.

17. The process of claim 6 wherein step (a) is carried out at elevated temperature to increase the separation factor.

* * * * *